(12) United States Patent  
Vlach

(10) Patent No.: US 9,021,165 B2  
(45) Date of Patent: Apr. 28, 2015

(54) CONNECTOR INTERFACE SYSTEM FOR DATA ACQUISITION

(71) Applicant: CardioNet, Inc., Malvern, PA (US)

(72) Inventor: Erich Vlach, San Diego, CA (US)

(73) Assignee: Braemar Manufacturing, LLC, Eagan, MN (US)

( * ) Notice: Subject to any disclaimer, the term of this patent is extended or adjusted under 35 U.S.C. 154(b) by 0 days.

(21) Appl. No.: 14/305,545

(22) Filed: Jun. 16, 2014

(65) Prior Publication Data

US 2014/0357132 A1 Dec. 4, 2014

Related U.S. Application Data

(63) Continuation of application No. 13/408,945, filed on Feb. 29, 2012, now Pat. No. 8,782,308.

(51) Int. Cl.
*G06F 13/38* (2006.01)
*A61B 5/024* (2006.01)
*H01R 13/642* (2006.01)
*G06F 19/00* (2011.01)
*G06F 3/06* (2006.01)
*H01R 27/00* (2006.01)

(52) U.S. Cl.
CPC .......... *G06F 13/385* (2013.01); *A61B 5/02438* (2013.01); *H01R 13/642* (2013.01); *G06F 19/3406* (2013.01); *A61B 2560/0456* (2013.01); *A61B 2562/226* (2013.01); *H01R 27/00* (2013.01)

(58) Field of Classification Search
None
See application file for complete search history.

(56) References Cited

U.S. PATENT DOCUMENTS

| | | |
|---|---|---|
| 5,678,562 A | 10/1997 | Sellers |
| 6,117,077 A | 9/2000 | Del Mar et al. |
| 6,223,080 B1 | 4/2001 | Thompson |
| 6,976,958 B2 | 12/2005 | Quy |
| 7,361,188 B2 | 4/2008 | Barr |

(Continued)

FOREIGN PATENT DOCUMENTS

GB 2475091 A 5/2011

OTHER PUBLICATIONS

Mokhbery, J., "USB Interface Simplifies Sensory Connections", Design News, Jun. 13, 2010, retrieved from the internet: htt;://www.designnews.com/document.asp?doc_id229070 (retrieved on Nov. 5, 2012).

(Continued)

*Primary Examiner* — Scott Sun
(74) *Attorney, Agent, or Firm* — Ropes & Gray LLP

(57) ABSTRACT

A data acquisition system includes a receptacle and a data acquisition device. The receptacle has a housing, sensor inputs to receive data signals from sensors coupled to an object, and a rib to block insertion of a standard Universal Serial Bus (USB) plug and facilitate insertion of a modified USB plug having a slot that mates with the rib. The data acquisition device includes circuitry to receive, store and process data, a USB plug having pins operatively coupled to the circuitry, a first subset of pins configured to receive data signals from the receptacle and a second subset of pins configured to support standard USB communication with USB-compliant devices, and a slot formed in the USB plug such that the slot facilitates interconnection of the USB plug both with standard USB-compliant devices and with the receptacle, the slot mating with the rib to facilitate interconnection.

20 Claims, 5 Drawing Sheets

(56) References Cited

U.S. PATENT DOCUMENTS

| | | |
|---|---|---|
| 7,598,878 B2 | 10/2009 | Goldreich |
| 7,615,007 B2 | 11/2009 | Shults et al. |
| 7,794,406 B2 | 9/2010 | Reisfeld et al. |
| 2003/0028442 A1 | 2/2003 | Wagstaff et al. |
| 2004/0229478 A1 | 11/2004 | Chen |
| 2005/0059301 A1 | 3/2005 | Chou et al. |
| 2005/0251003 A1 | 11/2005 | Istvan et al. |
| 2005/0251055 A1 | 11/2005 | Zhirnov et al. |
| 2006/0100530 A1 | 5/2006 | Kliot et al. |
| 2006/0149594 A1 | 7/2006 | Hilligoss et al. |
| 2006/0288147 A1 | 12/2006 | Hsieh |
| 2007/0142738 A1 | 6/2007 | Hung |
| 2007/0167694 A1 | 7/2007 | Causevic et al. |
| 2007/0197878 A1 | 8/2007 | Shklarski |
| 2007/0265541 A1 | 11/2007 | Hung |
| 2008/0026640 A1 | 1/2008 | Zheng et al. |
| 2008/0218799 A1 | 9/2008 | Hiew et al. |
| 2008/0234592 A1 | 9/2008 | Lim et al. |
| 2008/0243020 A1 | 10/2008 | Chou |
| 2009/0049213 A1* | 2/2009 | Chen .............................. 710/104 |
| 2009/0326612 A1 | 12/2009 | Distler |
| 2010/0004522 A1 | 1/2010 | Varela |
| 2010/0099954 A1 | 4/2010 | Dickinson et al. |
| 2010/0268103 A1 | 10/2010 | McNamara et al. |
| 2011/0160553 A1 | 6/2011 | Talbot et al. |
| 2012/0108934 A1 | 5/2012 | Valdes et al. |
| 2012/0289069 A1* | 11/2012 | Chueh et al. .................. 439/135 |

OTHER PUBLICATIONS

Copenhea Ver, Blaine, Authorized Officer, PCT Office, PCT International No. PCT/US2011/058976, in International Search Report, mailed Mar. 7, 2012, 14 pages.

Copenhea Ver, Blaine, Authorized Officer, PCT Office, PCT International No. PCT/US2011/058998, in International Search Report, mailed Mar. 12, 2012, 11 pages.

International Search Report and Written Opinion for PCT/US2012/030355 dated Nov. 28, 2012.

* cited by examiner

CONNECTOR INTERFACE SYSTEM FOR DATA ACQUISITION

CROSS REFERENCE TO RELATED APPLICATIONS

This application is a continuation application of U.S. patent application Ser. No. 13/408,945, filed on Feb. 29, 2012, which is hereby incorporated herein by reference in its entirety.

BACKGROUND

Generally speaking, a sensor is a device that measures an observable attribute and converts it into one or more electrical signals which can be recorded and/or subsequently (or concurrently) evaluated by another device (e.g., a computer system) and/or a human observer. Sensors are routinely used both to acquire biometric data (e.g., from a human test subject) and non-biometric data to measure attributes such as temperature, wind speed, humidity, salinity, barometric pressure, sound, light, and the like.

Biometric data often is acquired using appropriate sensors attached to a human subject to evaluate physiological activity of various organs, such as the heart or brain. The biometrics, data so acquired can be analyzed to look for patterns that may assist in diagnosing various conditions. For example, the electrical activity of the heart can be monitored to track various aspects of the functioning of the heart. Cardiac electrical activity can be indicative of disease states or other physiological conditions ranging from benign to fatal. Many other types of biometric data are routinely acquired and used by clinicians to assess health related factors.

SUMMARY

This document describes systems and techniques by which a connector interface system is used to acquire data—either biometric data or non-biometric data—from a sensor. For example, non-biometric data corresponding to a property such as salinity of sea water may be acquired from a salinity measuring instrument and recorded for later analysis with other oceanographic data. Similarly, biometric data corresponding to a physiological characteristic such as cardiac activity or the like may be acquired from an individual (e.g., a patient, test subject or other user) and analyzed or otherwise used by human or a machine—for example, a health care professional and/or a remote data processing center. For example, a subject can be provided with a biometric data acquisition device such as a real time monitoring device for monitoring a physiological signal for events (e.g. arrhythmia events, QRS data, etc.), a recording device, or essentially any other suitable electronic device. The biometric data acquisition device can obtain, for example, ECG data from the subject for a predefined period of time and can store the ECG data on a storage medium in the biometric data acquisition device.

As described in more detail below, the biometric data acquisition device optionally may include a data connector such as a USB connector (e.g., based on the USB 3.0 standard) so the subject can directly connect the biometric data acquisition device to a computer system such as the subject's personal computer. Alternatively, or in addition, the biometric data acquisition device can transfer or otherwise communicate the acquired data wirelessly or essentially in any other appropriate manner. Also, the biometric data acquisition device may be provided with program code that allows the subject to automatically upload the obtained biometric data to a remote data processing center when the biometric data acquisition device is connected to a computer using the USB connector.

The uploaded data can be analyzed by a computer running an analysis program at the remote data processing center. A medical professional, such as a doctor or a technician, can provide feedback regarding the analysis. Based on the analysis and the feedback, a report can be provided to the subject from the data processing center indicating the extent to which abnormal and/or clinically significant events were detected during the predefined period of time. The report can also include a recommendation to consult further with a physician based on clinically significant events identified in the uploaded data.

Implementations of the subject matter described in this document may include various combinations of the following features.

In an implementation, a data acquisition device may include circuitry configured to receive data (e.g., either biometric data and/or non-biometric data) acquired from one or more sensors coupled to an object (e.g., either a living subject or a non-living, electrically sensitive object), a Universal Serial Bus (USB) plug (e.g., a USB 3.0 Type-A connector) having a pins operatively coupled to the circuitry, a first subset of pins (e.g., pins 5-9 of the USB 3.0 Type-A connector) configured to receive data signals from the one or more sensors coupled to the object and a second subset of pins (e.g., pins 1-4 of the USB 3.0 Type-A connector) configured to support standard USB communication with USB-compliant devices, a modification to the USB plug configured such that the modification facilitates interconnection of the USB plug both with standard. USB-compliant devices and with an object-connected receptacle that is configured to prevent interconnection with standard USB plugs.

The modification formed in the USB plug may be a slot that mates with an accommodating feature in the object-connected receptacle. For example, the slot may be formed symmetrically in at least one of the USB plug's top and bottom sides. The data acquisition device may further include circuitry to store, process and/or transmit the acquired data.

In an implementation, a data acquisition receptacle may include sensor inputs configured to receive data signals (e.g., either biometric data signals and/or non-biometric data signals) from one or more sensors coupled to an object (e.g., either a living subject or a non-living, electrically sensitive object), and a connection prevention mechanism (e.g., a rib formed along a center portion of the receptacle) that is configured to prevent insertion of a standard USB plug and to facilitate insertion of and electrical connection with a modified USB plug having a feature that defeats the connection prevention mechanism (e.g., a slot that mates with the rib when the modified USB plug is inserted into the receptacle). The receptacle may further include either or both of a recess to receive the modified USB plug, and a substrate configured to facilitate secure connection of the modified USB plug white inserted in the receptacle. Alternatively, the receptacle may be implemented in an unshrouded configuration that lacks a recess.

In an implementation a data acquisition system includes a receptacle and a data acquisition device. The receptacle may include a housing, sensor inputs configured to receive data signals (e.g., biometric and/or non-biometric data signals) from one or more sensors coupled to an object (e.g., either a living subject or a non-living, electrically sensitive object), and a rib that is configured to block insertion of a standard USB plug and to facilitate insertion of and electrical connection with a modified USB plug having a slot that mates with the rib when inserted. The data acquisition device may include circuitry configured to receive, store and/or process data received via the receptacle from the one or more sensors coupled to the object, a USB plug having pins operatively coupled to the circuitry, a first subset of pins configured to receive data signals from the receptacle and a second subset of pins configured to support standard USB communication with USB-compliant devices, and a slot formed in the USB plug such that the slot facilitates interconnection of the USB plug both with standard USB-compliant devices and with the receptacle, the slot mating with the rib to facilitate interconnection between the data acquisition device and the receptacle.

In an implementation, a method of acquiring data may include establishing a connection between a receptacle to an object from which data is to be acquired via one or more sensors (e.g., either a living subject or a non-living, electrically sensitive object), the receptacle having a connection prevention mechanism that prevents connection of a standard USB plug to the receptacle, connecting a data acquisition device having a modified USB plug to the receptacle having the connection prevention mechanism, the modified USB plug being configured such that the modification defeats the receptacle's connection prevention mechanism while facilitating interconnection of the modified USB plug with standard USB-compliant devices, and acquiring object-related data via the one or more sensors using the connected data acquisition device. Optionally, the method of acquiring data may further include disconnecting the data acquisition device by unplugging the modified USB plug from the receptacle having the connection prevention mechanism, and connecting the data acquisition device to an electronic device having a standard USB receptacle (e.g., a computer system).

Details of one or more implementations are set forth in the accompanying drawings and the description below. Other features, aspects, and potential advantages will be apparent from the description and drawings, and from the claims.

DESCRIPTION OF DRAWINGS

Like reference symbols in the various drawings indicate like elements.

DETAILED DESCRIPTION

Figure 1:
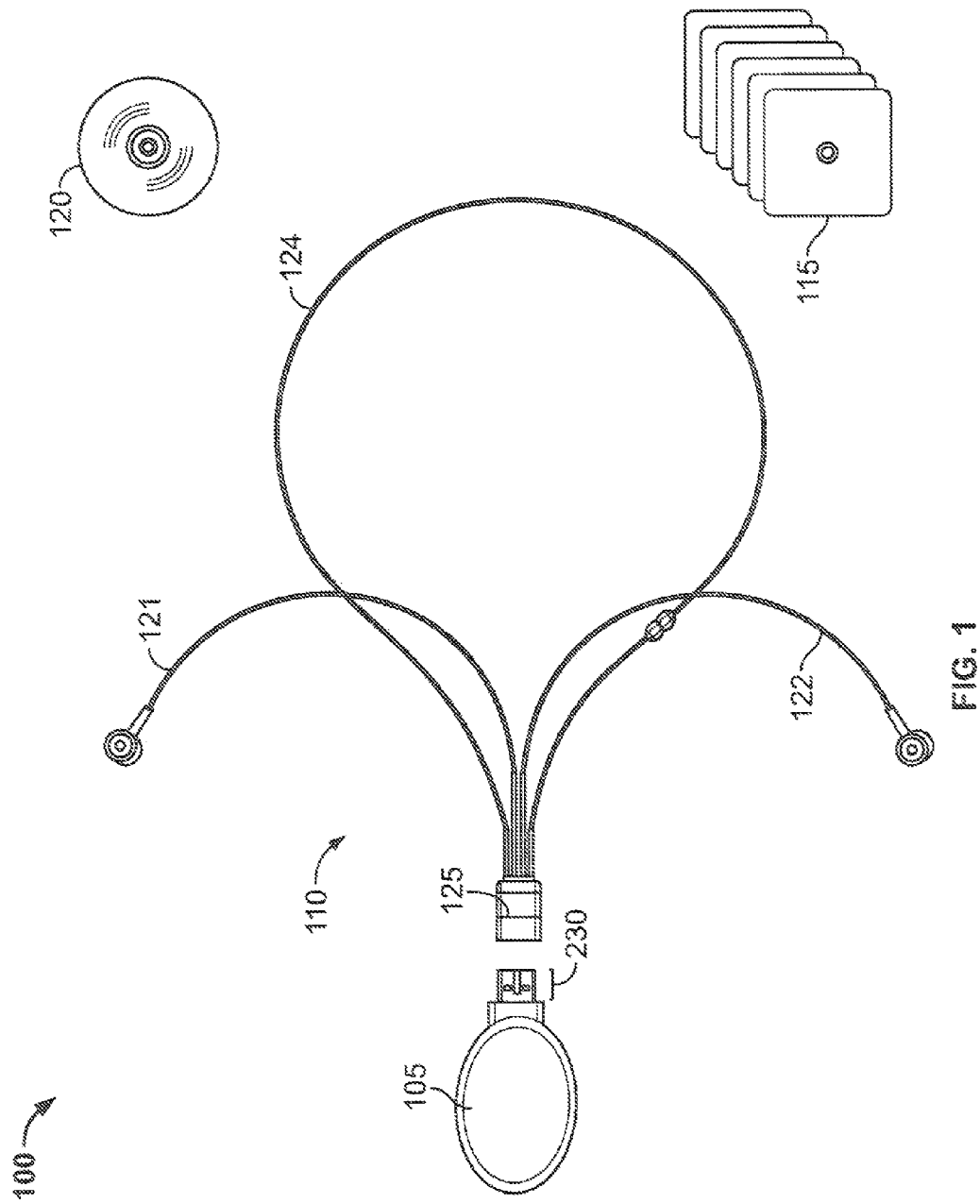
FIG. 1 shows an example of a self-assessment kit for obtaining ECG data from a subject.

FIG. 1 shows an example of a self-assessment kit for obtaining ECG data from a subject—that is, the object to which the sensors are connected is a human subject. The self-assessment kit includes a data acquisition unit 105 having a modified USB plug 230 and an object-connected receptacle 125 into which the modified USB plug can be inserted, and to which one or physiological sensors can be connected. One example of a physiological sensor is a lead-wire set 110 having, for example, a first electrode lead 121, and a second electrode lead 122, which may be used to obtain ECG signals from the subject. Alternatively, the object-connected receptacle 125 may be connected to essentially any other appropriate physiological sensor that can sense biometric data from a subject (e.g., blood pressure sensor, pulse oximeter, glucometer or the like).

When it is desired to acquire ECG data from a subject, the kit also may include electrodes 115 in the form of removable electrode patches, and program code 120 stored on a medium such as a CD-ROM. The self-assessment kit allows a subject to obtain his or her own ECG signal, upload ECG data to a remote data processing center, and obtain an assessment from the data processing center without the need to involve a third-party medical practitioner such as a prescribing physician. Also, the self-assessment kit can be configured to allow a subject to self-monitor his or her own ECG signal for a specified period of time such as 14 days.

The object-connected receptacle 125 is configured to be insertably connectable, via the modified USB plug 230, to the data acquisition unit 105. When connected, the data acquisition unit 105 can be hung from the neck of the subject using a lanyard 124 on the lead-wire set 110. The object-connected receptacle 125 also includes contacts that, when connected to the data acquisition unit 105, form electrical connections to corresponding contacts within the data acquisition unit 105 thereby enabling the data acquisition unit 105 to receive electrical signals emanating from the electrodes 115.

The electrodes 115 can be disposable electrode patches that can be connected to distal ends of the first electrode lead 121 and the second electrode lead 122. The electrodes 115 have adhesive backing so that they can be stuck to the chest of the subject. The self-assessment kit can include enough disposable electrodes 115 for the specified period of time.

While being used to acquire biometric data from a subject, the data acquisition unit 105 is connected to the object-connected receptacle 125, and one of the electrode patches is connected to the first electrode lead 121 and another of the electrode patches is connected to the second electrode lead 122. The subject sticks the connected electrodes to his or her chest and wears the data acquisition unit 105 around his or her neck with the lanyard 124. The data acquisition unit 105 obtains an electrical signal from the electrode patches connected to the first electrode lead 121 and the second electrode lead 122. The electrical signal is converted to a digital signal and stored in the data acquisition unit 105 as ECG data.

Although the self-assessment kit shown in FIG. 1 is specific to the application of acquiring ECG data from the subject, other kits and configurations are possible to collect essentially any other appropriate type of physiological data from the subject, for example, electromyography (EMG) data, electroencephalography (EEG) data or the like.

Figure 2A:
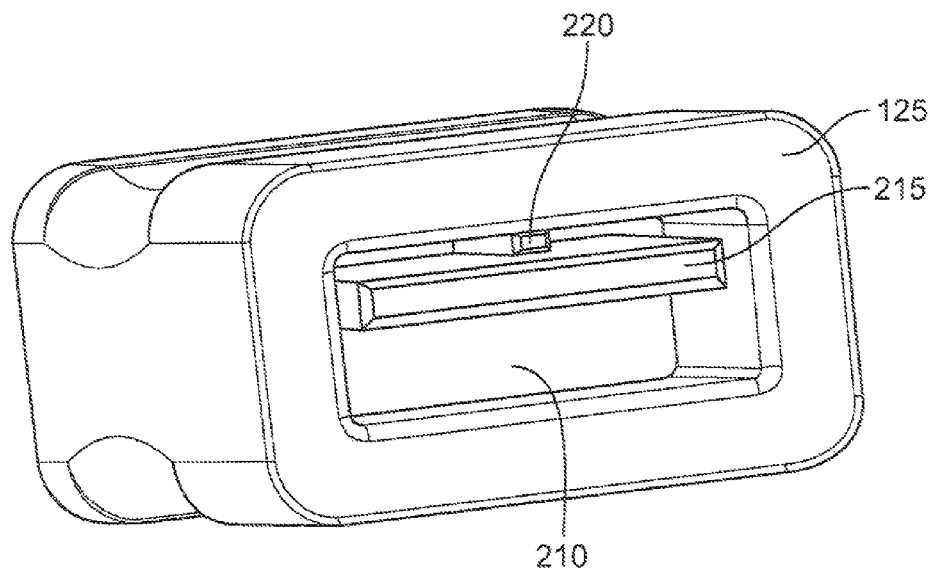
FIGS. 2A and 2B show perspective views of an object-connected receptacle and an acquisition device having a modified USB plug, respectively.
Figure 2B:
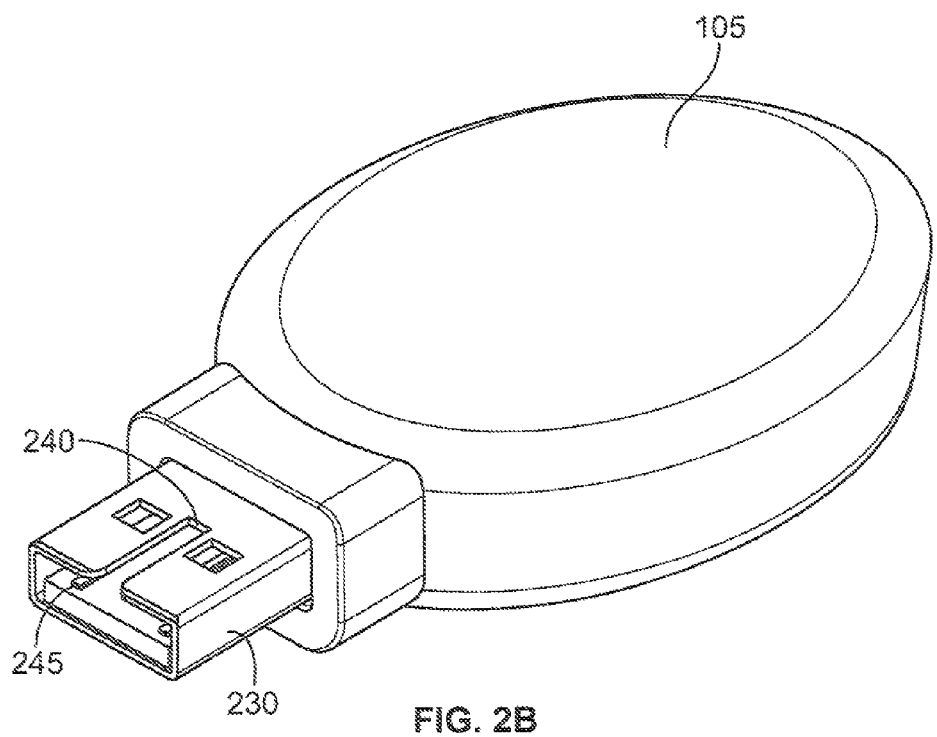

FIGS. 2A and 2B show perspective views of an example implementation of the object-connected receptacle 125 and the data acquisition unit 105 having a modified USB plug 230, respectively. As shown therein, the object-connected receptacle 125 includes a recess 210 in which a contact substrate 215 and a rib 220 are formed or otherwise disposed. The configuration of receptacle 125 shown in FIG. 2A is exemplary and could be implemented in other configurations depending on application and/or design criteria. For example, the receptacle 125 could be implemented in an unshrouded configuration that does not include a recess 210 formed by sidewalls of the receptacle 125.

Although the form and dimensions of the recess 210 are designed to accommodate a Universal Serial Bus (USB) connector, the presence of the rib 220 prevents a standard USB connector from being plugged into the object-connected receptacle 125. In other words, the rib 220 acts as a connection prevention mechanism that effectively prevents a standard, non-modified USB plug from being inserted into the receptacle 125 to the point where electrical contact is made between one or more conductors of the USB plug and one or more conductors of the receptacle 125. Consequently, the object is protected from potential harm that might arise, for example, if the object-connected receptacle 125, while connected to biometric sensors on a human subject's body or non-biometric sensors on an electrically sensitive measurement instrument, was connected to a standard USB connector that in turn was connected to a power source and thus could apply a dangerous or destructive level of electrical current to the object—that is, to the human subject's body or to the measurement instrument, depending on the particular application. By including the rib 220 in the recess 210, the object-connected receptacle prevents this potential electrical safety hazard.

The receptacle 125 shown in FIG. 2A can be used as a connection interface for essentially any type of data sensor—either biometric or non-biometric. Regardless of the particular type of sensor involved, the receptacle 125 is configured to prevent connection to a standard USB connector, thereby protecting the sensor (and/or potentially also whatever the sensor is connected to) from harm that might arise from being connected to a power source.

As shown, the data acquisition unit 105 shown in FIG. 2B includes a modified USB plug 230 having a slot 240 and pins 245. The slot 240 in the plug 230 and the rib 220 in the object-connected receptacle 125 are formed such that the rib 220 suitably fits within the slot 240 when the plug 230 is inserted into the recess 210 of the object-connected receptacle 125. When inserted, the rib 220 mates with the slot 240 and the pins 245 of the plug 230 form electrical connections with corresponding contacts within the object-connected receptacle 125, for example, formed along tab 215 thereby enabling the data acquisition unit 105 to acquire data from the object (or subject, if the object is a human or other living organism) via whatever sensors happen to be connected to the object-connected receptacle 125.

In the illustrated implementation, the plug 230 on the data acquisition unit 105 is a modified USB connector, in this example, a USB connector based on the USB Type-A standard. The plug 230 is modified from the USB Type-A standard, however, in that it includes slot 240, which is not present in conventional USB connectors. The presence of slot 240 enables the plug 230 to be connected to the object-connected receptacle 125, which includes rib 220 and which, as noted above, prevents standard, unmodified USB connectors from being inserted into the object-connected receptacle 125. The presence of slot 240, however, does not affect the ability of the plug 230 from being inserted and fitting within a standard USB receptacle that lacks the rib 220. Consequently, because only a single type of connector is needed—namely, a USB Type-A plug modified to have a slot 240—both to connect to the object-connected receptacle 125 and to standard computer equipment, the number of required connection types is minimized, thereby increasing simplicity and efficiency, and reducing time and costs, both in the manufacturing and end-user contexts.

Depending on the desired application, the plug 230 also may vary from the USB standard in the particular pin connections used. Specifically, if the USB 3.0 standard is used (which provides 9 conductors instead of 4 conductors used in USB 1.0 and 2.0 standards), the plug 230 can use pins 5-9 of the USB 3.0 Type-A connector for connecting to corresponding contacts in the object-connected receptacle 125 and thereby to receive data from sensors attached to the object. In such an implementation, pins 1-4 of the plug 230 are configured to comply with the conventional USB 1.x and USB 2.x standards. Consequently, this modified usage of pins enables the plug 230 to serve dual purposes—that is, it can both connect to the object-connected receptacle 125 to receive data from an object and, once disconnected from the object-connected receptacle 125, it can then be inserted in any standard computer system or other electronic equipment having USB 1.x and/or USB 2.x connectivity to transfer the acquired data to the desired destination and/or to be used as input to an analysis program running on the computer system.

Figure 3A:
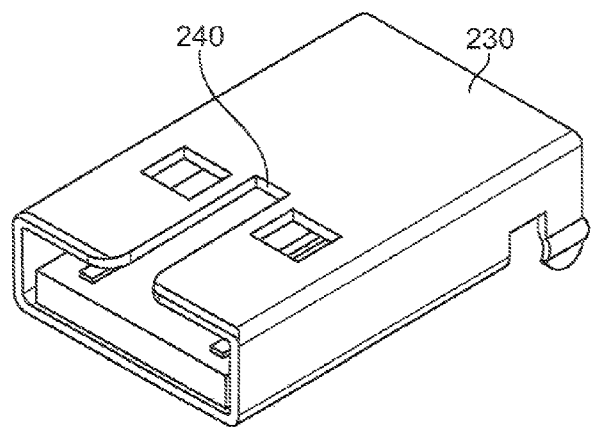
FIGS. 3A, 3B and 3C are various views of a modified USB plug.
Figure 3B:
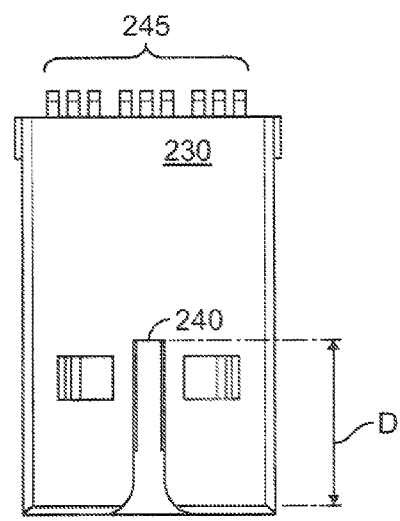
Figure 3C:
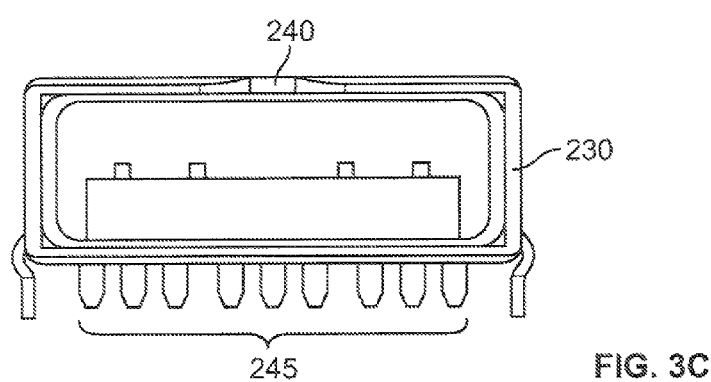

FIGS. 3A, 3B and 3C show perspective, top planar and front planar views, respectively, of a modified USB 3.0 Type-A connector that may be used for plug 230 on data acquisition unit 105. As shown therein, the slot 240 is formed in the center of the plug 230 but, depending on other factors, potentially could be offset to one side or the other (but requiring a corresponding change to the relative location of rib 220 within the recess 210 of object-connected receptacle 125 to ensure that the rib 240 would appropriately mate with the slot 240). In addition, the slot 240 should be of sufficient depth, D (for example, in the range of 8-9 mm), such that the plug 230 can be fully inserted into the object-connected receptacle 125 to form reliable connections between pins 5-9 of the plug 230 and corresponding contacts residing within the object-connected receptacle 125.

Figure 4:
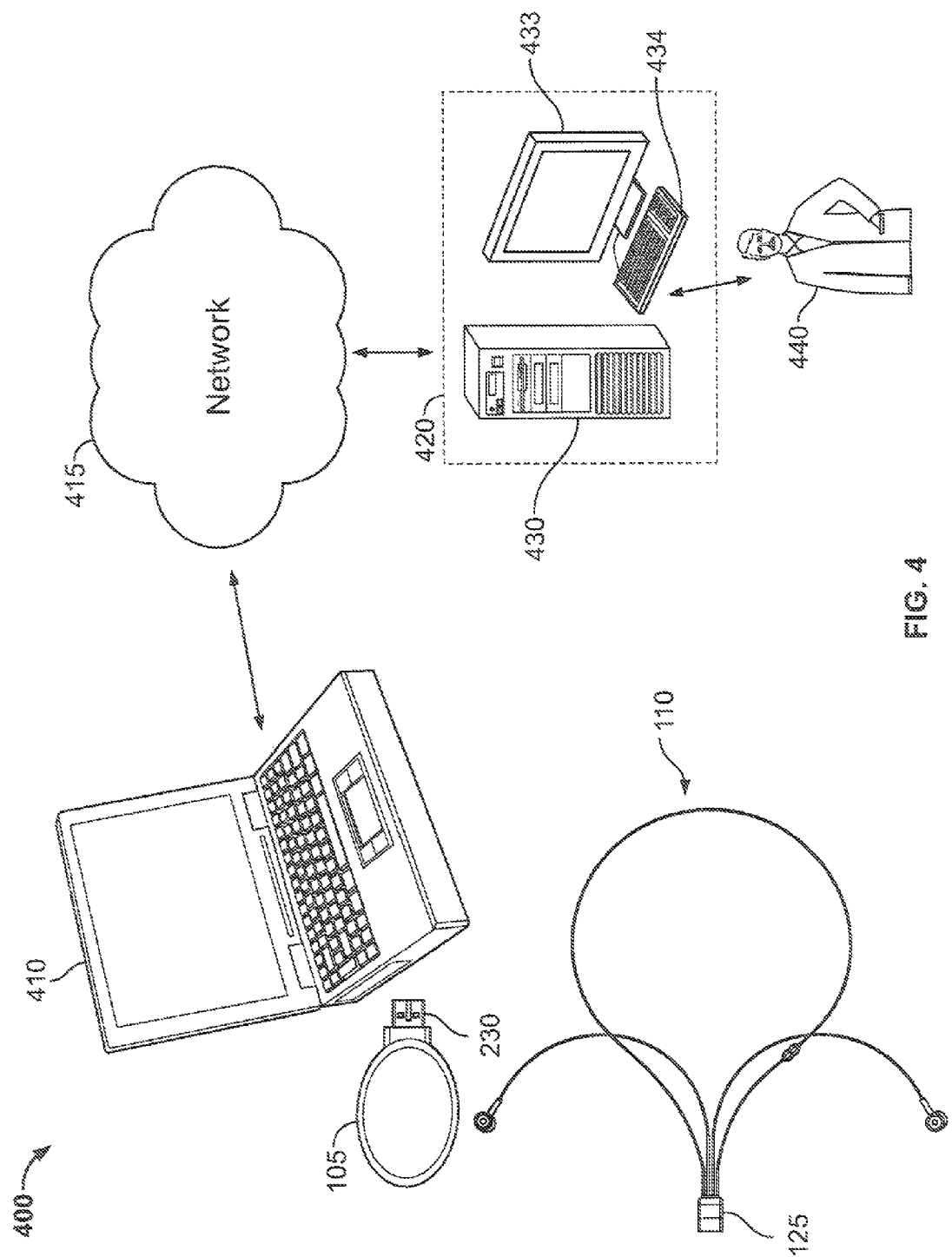
FIG. 4 shows an example system for uploading biometric data stored on a data acquisition unit.

FIG. 4 shows an example system 400 for uploading the ECG data stored on the data acquisition unit 105. The program code 120 can be run on a computer system 410 such as the subject's personal computer. The computer system 410 includes a computer and a display device. When the subject has completed the data acquisition period, the subject can disconnect the data acquisition unit 105 from the lead-wire set 110 and connect the USB plug 230 to the computer system 410. The program code when run by the computer system 410, supports access to a remote data processing center 420 so that the ECG data can be uploaded from the data acquisition unit 105 over a network 415 to the remote data processing center 420 where the biometric data is analyzed. The program code can support access to the remote data processing center 420 by automatically initiating a transmission of the ECG data stored on the data acquisition unit 105 upon detecting that the data acquisition unit 105 is connected to the computer system 410.

In some examples, the data processing center can obtain demographic or other clinically relevant data about the subject. This additional data can assist in the analysis of the biometric data obtained from the data acquisition unit. For example, a particular event detected in a physiological signal can be serious for one person and not serious for another based on demographics such as age. The program code, when run by the computer system 410, can also facilitate the data processing center in obtaining clinically relevant data about the subject.

In some examples, the computer 410 can include a public terminal such as a kiosk specifically provided for obtaining the subject data from the data acquisition unit and uploading the subject data to the data processing center 420. The public terminal is provided in a public location such as in a health care facility like a doctor's office, a pharmacy, or the like. The public terminal can be pre-loaded with a program for obtaining the data from the data processing device and uploading the data over the network 415 to the data processing center 420. The public terminal can also be configured to obtain the demographic information from the subject when the subject uploads the data. A report from the data processing center 420 can be viewed or printed directly from the public terminal.

In some examples, the subject can provide the data acquisition unit 110 to a third-party for uploading the data to the data processing center 420. For example, the self-assessment kit can include a pre-paid package for mailing the data acquisition unit 110 to a third-party or directly to the data processing center. The kit can also include a questionnaire for the subject to fill-out to provide demographic data to facilitated analysis by the data processing center 420 and to provide a location for a report to be sent to the subject either by mail or electronically.

Figure 5:
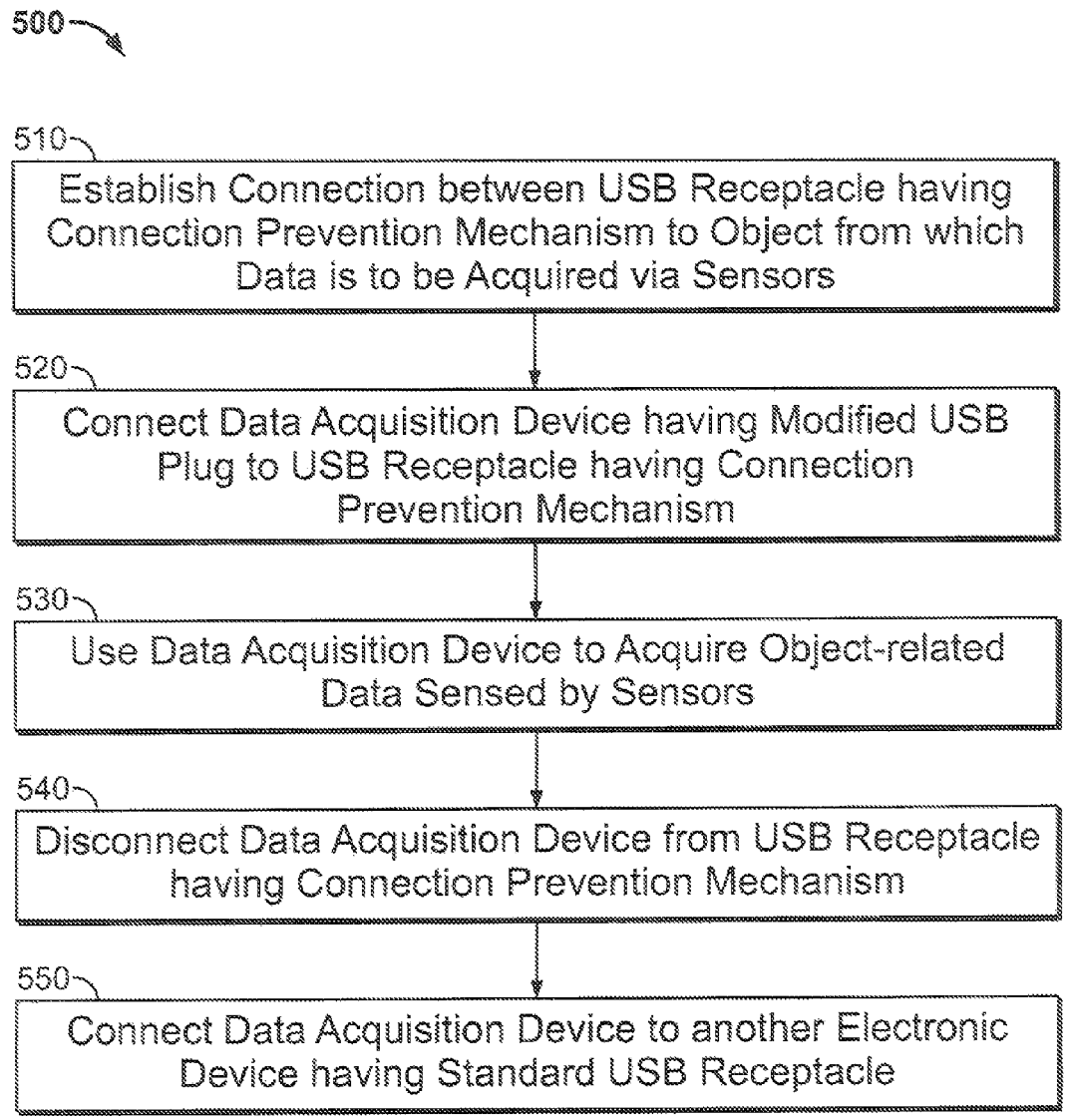
FIG. 5 shows an exemplary method for acquiring data relating to an object, via sensors coupled to the object, using a modified USB plug and an object-connected USB receptacle having a connection prevention mechanism.

FIG. 5 shows an exemplary method for acquiring data relating to an object, via sensors coupled to the object, using a modified USB plug and an object-connected USB receptacle having a connection prevention mechanism. This method, and/or variations thereof, can be used to acquire data (either biometric or non-metric) from an object (either a human or other biological subject or a non-living object) using a USB-type connectors, the prevalence of which are widespread in the science and engineering worlds, while effectively protecting the object from potentially damaging electrical currents and/or voltages to which the object might otherwise be exposed.

As shown in FIG. 5, at 510, an electrical connection is established between a USB receptacle having a connection prevention mechanism (e.g., a rib 220 such as shown in FIG. 2A) and, using suitable sensors, an object (e.g., a human subject or an inanimate object that has measurable properties) about which data is to be acquired.

Next, at 520, a data acquisition device (e.g., a data recorder, processor and/or transmitter) having a modified USB plug (e.g., modified with a slot 240 that mates with rib 220 on the receptacle, such as shown in FIGS. 2B and 2A, respectively) is inserted into the USB receptacle to form an electrical connection. Even though the USB receptacle has a connection prevention mechanism, the modified USB plug is able to be inserted into and form an electrical connection with the USB receptacle because the modifications to the USB plug are such that they are complementary, and thus overcome, the obstacles to connection otherwise presented to standard USB plugs by the USB receptacle's connection prevention mechanism.

Next, at 530, the data acquisition device is operated to acquire the desired data from the object in question (and, depending on the device in question and the specific application, store the acquired data locally on the data acquisition device, process it in some manner, transmit it elsewhere, or any combination thereof). After completion of data acquisition, at 540, the data acquisition device is unplugged, and thus disconnected, from the USB receptacle having the connection prevention mechanism.

Optionally, depending on the specific application at hand, for example, if post-acquisition wired transmission of the acquired data is desired either instead of or in addition to prior or concurrent wireless transmission of the acquired data, the data acquisition device can then, at 550, be plugged into essentially any other electronic device (e.g. a computer system) so that the data stored thereon can be transferred to, or processed by that other electronic device. Note that the modifications to the modified USB plug used by the data acquisition device are such as not to interfere with standard mechanical or electrical connections when the modified USB plug is inserted into any standard electronic device that follows the USB 1.x and/or USB 2.x standards.

The disclosed systems, techniques, and all of the functional operations described and illustrated in this specification can be implemented in digital electronic circuitry, or in computer hardware, firmware, software, or in combinations of the forgoing. For example, one or more computers and/or circuitry can be operable to or configured and arranged to perform the functions and techniques disclosed herein. Apparatuses and/or systems can be implemented using a software product (e.g., a computer program code) tangibly embodied in a machine-readable storage device for execution by a programmable processor, and processing operations can be performed by a programmable processor executing a program of instructions to perform functions by operating on input data and generating output. Further, the system can be implemented advantageously in one or more software programs that are executable on a programmable system. This programmable system can include the following: 1) at least one programmable processor coupled to receive data and instructions from, and to transmit data and instructions to, a data storage system; 2) at least one input device; and 3) at least one output device. Moreover, each software program can be implemented in a high-level procedural or object-oriented programming language, or in assembly or machine language if desired; and in any case, the language can be a compiled or an interpreted language.

Also, suitable processors include, by way of example, both general and special purpose microprocessors. Generally, a processor will receive instructions and data from a read-only memory, a random access memory, and/or a machine-readable signal (e.g., a digital signal received through a network connection). The essential elements of a computer are a processor for performing instructions and one or more memory devices for storing instructions and data. Generally, a computer wilt include one or more mass storage devices for storing data files. Such devices can include magnetic disks, such as internal hard disks and removable disks, magneto-optical disks, and optical disks. Storage devices suitable for tangibly embodying software program instructions and data include all forms of non-volatile memory, including, by way of example, the following: 1) semiconductor memory devices, such as EPROM (electrically programmable read-only memory); EEPROM (electrically erasable programmable read-only memory) and flash memory devices; 2) magnetic disks such as internal hard disks and removable disks; 3) magneto-optical disks; and 4) CD-ROM disks. Any of the foregoing can be supplemented by, or incorporated in, ASICs (application-specific integrated circuits).

The disclosed systems and techniques, described and illustrated in this specification can be implemented using a communications network such as a wired or wireless network. Examples of communication networks include, e.g., a local area network ("LAN"), a wide area network ("WAN"), the Internet or any combinations of such.

To provide for interaction with a user (such as the health care provider), systems can be implemented on a computer system having a display device such as a monitor or LCD (liquid crystal display) screen for displaying information to the user and a keyboard and a pointing device such as a mouse or a trackball by which the user can provide input to the computer system. The computer system can be programmed to provide a graphical user interface through which computer programs interact with users.

A number of embodiments have been described. Nevertheless, it will be understood that various modifications may be made without departing from the spirit and scope of the invention. Accordingly, other embodiments are within the scope of the following claims.

What is claimed is:

1. A data acquisition device comprising:
   circuitry configured to receive data acquired from one or more sensors coupled to an object;
   a Universal Serial Bus (USB) plug having a plurality of pins operatively coupled to the circuitry, a first subset of the plurality of pins configured to receive data signals from the one or more sensors coupled to the object and a second subset of the plurality of pins configured to support standard USB communication with USB-compliant devices; and
   a modification to the USB plug configured such that the modification facilitates interconnection of the USB plug both with standard USB-compliant devices and with an object-connected receptacle that is configured to prevent interconnection with standard USB plugs.

2. The device of claim 1 in which the USB plug comprises a USB 3.0 Type-A connector.

3. The device of claim 2 in which the first subset of the plurality of pins comprises pins 5-9 of the USB 3.0 Type-A connector and the second subset of the plurality of pins comprises pins 1-4 of the USB 3.0 Type-A connector.

4. The device of claim 1 in which the modification formed in the USB plug comprises a slot that mates with an accommodating feature in the object-connected receptacle.

5. The device of claim 4 in which the USB plug has top and bottom sides, and the slot is formed symmetrically in at least one of the USB plug's top and bottom sides.

6. The device of claim 1 in which the object comprises a living subject and the device is configured to acquire biometric data from the living subject.

7. The device of claim 1 in which the object comprises an electrically sensitive object and the device is configured to acquire non-biometric data from the electrically sensitive object.

8. The device of claim 1 further comprising circuitry to store, process and/or transmit the acquired data.

9. A data acquisition receptacle comprising:
   a plurality of sensor inputs configured to receive data signals from one or more sensors coupled to an object; and
   a connection prevention mechanism that is configured to prevent insertion of a standard Universal Serial Bus (USB) plug and to facilitate insertion of and electrical connection with a modified USB plug having a feature that defeats the connection prevention mechanism.

10. The receptacle of claim 9 in which the connection prevention mechanism comprises a rib.

11. The receptacle of claim 10 in which the feature of the modified USB plug that defeats the receptacle's connection prevention mechanism comprises a slot that mates with the rib when the modified USB plug is inserted into the receptacle.

12. The receptacle of claim 10 in which the rib is formed along a center portion of the receptacle.

13. The receptacle of claim 10 further comprising a substrate configured to facilitate secure connection of the modified USB plug while inserted in the receptacle.

14. The receptacle of claim 9 further comprising a recess to receive the modified USB plug.

15. The receptacle of claim 9 in which the receptacle is formed in an unshrouded configuration that lacks a recess.

16. A method of acquiring data, the method comprising:
    establishing a connection between a receptacle to an object from which data is to be acquired via one or more sensors, the receptacle having a connection prevention mechanism that prevents connection of a standard USB plug to the receptacle;
    connecting a data acquisition device having a modified USB plug to the receptacle having the connection prevention mechanism, the modified USB plug being configured such that the modification defeats the receptacle's connection prevention mechanism while facilitating interconnection of the modified USB plug with standard USB-compliant devices; and
    acquiring object-related data via the one or more sensors using the connected data acquisition device.

17. The method of claim 16 further comprising:
    disconnecting the data acquisition device by unplugging the modified USB plug from the receptacle having the connection prevention mechanism; and
    connecting the data acquisition device to an electronic device having a standard USB receptacle.

18. The method of claim 17 wherein the electronic device having the standard USB receptacle comprises a computer system.

19. The method of claim 16 in which the object comprises a living subject and the method acquires biometric data from the living subject.

20. The method of claim 16 in which the object comprises an electrically sensitive object and the method acquires non-biometric data from the electrically sensitive object.

* * * * *